(12) United States Patent
Lindqvist et al.

(10) Patent No.: US 7,416,847 B1
(45) Date of Patent: Aug. 26, 2008

(54) IN VITRO PEPTIDE OR PROTEIN EXPRESSION LIBRARY

(75) Inventors: Bjorn H. Lindqvist, Oslo (NO); David Andrews, Hamilton (CA); Elizabeth Haggard-Ljungquist, Stockholm (SE); Morten Isaksen, Siljan (NO)

(73) Assignee: Isogenica Limited, Peterborough (GB)

( * ) Notice: Subject to any disclaimer, the term of this patent is extended or adjusted under 35 U.S.C. 154(b) by 0 days.

(21) Appl. No.: 09/331,808

(22) PCT Filed: Feb. 18, 1998

(86) PCT No.: PCT/GB98/00518

§ 371 (c)(1),
(2), (4) Date: Jan. 27, 2000

(87) PCT Pub. No.: WO98/37186

PCT Pub. Date: Aug. 27, 1998

(30) Foreign Application Priority Data

Feb. 18, 1997 (GB) ................................. 9703369.0

(51) Int. Cl.
*G01N 33/53* (2006.01)
*C40B 30/04* (2006.01)

(52) U.S. Cl. ............ 435/7; 435/6; 435/5; 435/DIG. 15; 435/DIG. 14

(58) Field of Classification Search ...................... 435/6, 435/5, 4, 320.1, DIG. 2, 3, DIG. 14, DIG. 15; 435/7.1; 530/350; 536/23.1, 23.5, 24.2, 536/24.3, 25.3
See application file for complete search history.

(56) References Cited

U.S. PATENT DOCUMENTS

| | | | | |
|---|---|---|---|---|
| 5,498,530 A | * | 3/1996 | Schatz et al. ................ | 435/69.1 |
| 5,627,024 A | * | 5/1997 | Maruyama et al. ............. | 435/5 |
| 5,922,545 A | * | 7/1999 | Mattheakis et al. ............ | 425/6 |
| 6,100,035 A | * | 8/2000 | Kauffman et al. .............. | 435/6 |
| 7,138,511 B1 | * | 11/2006 | Nguyen et al. ............. | 536/23.5 |

OTHER PUBLICATIONS

Masai et al, Nucleic acdis rEsearch, 16(14)1988, 6493-14.*
Derbyshire et al, Molecular Microbiology, 1261-72, 1996.*
Dubeau and Denhardt, "The Mechanism of Replication of ΦX174 XVIII. Gene A and A* Proteins of ΦX174 Bind Tightly to ΦX174 Replicative Form DNA", Biochimica et Biophysica Acta 653:52-60 (1981).
FitzGerald, "In vitro display technologies—new tools for drug discovery", DDT 5(6):253-258 (2000).

* cited by examiner

*Primary Examiner*—T. D. Wessendorf
(74) *Attorney, Agent, or Firm*—Nixon & Vanderhye P.C.

(57) ABSTRACT

The present invention relates to methods of producing peptide or protein expression libraries. In such a library, a population of nucleotide sequences is expressed. The resulting peptides or proteins encoded by those nucleotide sequences are then screened to identify those peptides or proteins having a desired property such as the ability to bind a selected ligand. In the construction and screening of such libraries, it is desired to ensure that the nucleotide encoding a particular protein remains connected in some way with that protein so that once a desired protein having a selected property has been isolated, its encoding nucleotide sequence may be specifically recovered for subsequent manipulation for example using PCR or sequencing. The present invention makes use of a property not previously described in constructing an expression library namely the use of proteins which covalently bind DNA. DNA is expressed in such a way that the protein so expressed binds to its own encoding DNA therefore allowing the DNA to be associated only with its encoding protein.

13 Claims, 2 Drawing Sheets

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
gcgcctcgga gtcctgtcaa                                                    20

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
agcggcatcg ccgcgcctcg gagtcctgtc                                         30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
gacaggatct tagaatgcgg cgatgccgct                                         30

<210> SEQ ID NO 4
<211> LENGTH: 135
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: unsure
<222> LOCATION: 88, 89, 91, 92, 94, 95, 96, 98, 99, 101, 102, 104, 105,
      106, 108, 109, 111, 112, 114, 115, 116
<223> OTHER INFORMATION: "n" can be A, T, G or C

<400> SEQUENCE: 4
gaaattaata cgactcacta tagggagacc acaacggttt ccctctagaa ataattttgt        60
ttaactttaa gaaggagata taccatgnnk nnknnnknnk nnknnnknnk nnknnnkgcc       120
gttaaagcct ccggg                                                       135

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
gaaattaata cgactcacta taggg                                              25

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
caaaaaaccc ctcaagaccc g                                              21

<210> SEQ ID NO 7
<211> LENGTH: 144
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: unsure
<222> LOCATION: 97, 98, 100, 101, 103, 104, 106, 107, 109, 110, 112,
      113, 115, 116, 118, 119, 121, 122, 124, 125
<223> OTHER INFORMATION: "n" can be A, T, G or C

<400> SEQUENCE: 7
cgatcccgcg aaattaatac gactcactat agggagacca caacggtttc cctctagaaa    60
taattttgtt taactttaag aaggagatat accatgnnkn nknnknnknn knnknnknnk   120
nnknnkgccg ttaaagcctc cggg                                          144

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 8
agatctcgat cccgcgaaat taatacgact cactataggg                          40
```

IN VITRO PEPTIDE OR PROTEIN EXPRESSION LIBRARY

Figure 1:
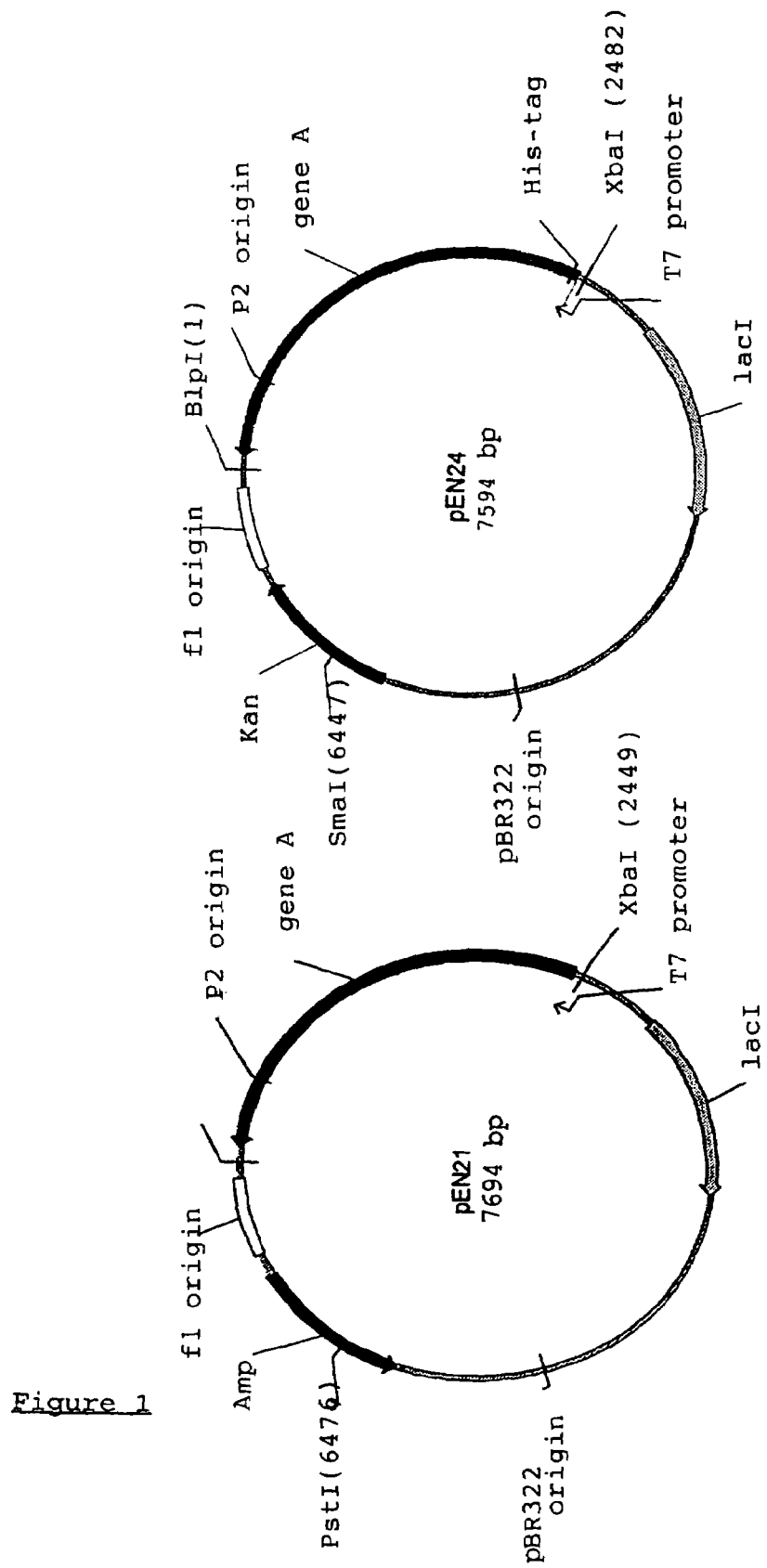

This application is the U.S. national phase of international application PCT/GB98/00518 filed Feb. 18, 1998, which designated the US ans which claims priority to UK Application No. GB9703369.0 filed Feb. 18, 1997.

The present invention relates to methods for producing an in vitro peptide or protein expression library which displays a diverse population of peptides or proteins, the expression library thus produced and use of the library to identify peptides or proteins exhibiting desired properties. The invention also relates to specific DNA sequences which include the coding region for the peptides or proteins and which bind specifically to their translation product by covalent attachment.

In the same way that libraries provide the reader with a vast collection of a variety of books which are retrievable, so too a molecular library provides a reference bank of molecules which may be selected and retrieved. Such libraries may contain genetic material, for example fragments of DNA sequences in a plasmid or bacteriophage, or express peptides or proteins encoded by the genetic material in the library. In the latter case to allow selection of the relevant member of the library, the expressed peptide or protein must necessarily associate with the genetic material which encodes it. Currently, this is achieved in a number of different ways.

Firstly, peptides may be displayed on the outer surfaces of genetic packages such as cells, viruses and spores, particularly bacteriophage, bacteria or yeast as fused parts of a display protein. The invariant moiety of the display protein in a particular library is selected to have the characteristic that it is expressed on the surface of the genetic package, for example a cell or virion and is stably associated with the cell or virion such that genetic packages expressing the target protein or peptide may be retrieved.

Smith and Scott (Smith (1985), Science, 228, p 1315-6; Scott and Smith (1990), Science, 249, p 386-390) describe the use of bacteriophage Fd as a display vector for a random sequence of peptides exposed on the virion surface. U.S. Pat. No. 5,223,409 of Ladner expresses families of potential binding domains on the outer surface of bacterial cells or bacteriophages. Other workers in many laboratories have similarly used such genetic packages for generating expression libraries. A lot of this work has been performed on filamentous phages like M13 which has proven to be a robust and relatively easy system to handle.

However, this technology still suffers from certain drawbacks, like the time and effort required to make a library that is large enough to produce enough variants for selection. Additionally, the genetic packages used thus far must be maintained in a viable state to allow both expression of the encoded protein or peptide and also propagation of the genetic package during successive screening steps. Furthermore, the polypeptide displayed must be compatible with export from the organism and assembly of the fusion partner into the appropriate structure on the organism. Also, since protein synthesis occurs in vivo, only those modifications that can be accomplished by the translation host can be incorporated into the displayed sequence.

The time involved in the propagation of selected genetic packages during the screening protocol also presents a significant time burden to the researcher. Furthermore, it is necessary in the currently used in vivo peptide display library to transfect the genetic material of the library into a host to allow replication and expression and transformation is known to be an inefficient procedure which therefore reduces the number of members that may be present in an expression library.

More recently, in vitro expression libraries have been described which overcome some of the above mentioned limitations of in vivo expression libraries. For example, polysome display has been described in which a correctly folded complete protein carrying different display peptides in different members of the library and its encoding mRNA both remain attached to the ribosomes. This is achieved by ensuring that the protein chain does not leave the ribosome and the mRNA does not leave the ribosome (ie. there is no stop codon and the ribosomes are stabilized). Such expression libraries are the subject of several patent applications, for example as published in WO92/02536 (The Regents of the University of Colorado), WO93/03172 (University Research Corporation) and WO91/05058 (Kawasaki).

Polysome libraries suffer from certain limitations. RNA is very sensitive to RNAses and is thus difficult to work with. To retain attachment of the ribosomes requires the continued presence of magnesium ions which creates problems for screening and other steps where it must always be present. Most importantly, all the steps after translation, especially during the screening and selection procedure, may not be performed with harsh reagents as the polysome:RNA link must be retained.

A different in vitro expression library which has been suggested involves the use of DNA-binding proteins. These proteins are expressed in a bacterium or other membrane delimited organism using a plasmid containing a binding site for the DNA-binding protein. The polypeptide and encoding nucleic acid are operatively linked since the protein transiently associates with the encoding nucleic acid. Library sequences are introduced into the polypeptide without affecting binding to DNA by insertion of the display moiety to yield a fusion protein. Such libraries are described in for example the international patent application published as WO93/08278 (Affymax Technologies NV).

Whilst such in vitro libraries have the advantage that screening may be performed in vitro, since the encoded fusion protein does not uniquely recognize its own encoding DNA (but rather recognizes and associates with its binding site on DNA wherever this appears) at least translation must be performed in vivo with only a single library member per host cell or organism. This severely restricts the complexity that the library may achieve. Thus some of the limitations of in vivo expression libraries, such as the inefficiency of transformation, are applicable. Furthermore, the association between the DNA-binding proteins and their attachment site on the DNA is not covalent, and there is thus an off-time associated with the interaction which may be in the order of only 30 minutes. Thus the time taken to perform screening steps post-translation must be kept as low as possible and the conditions of screening must be selected such that the off-rate is not further increased. Thus restrictive limitations still exist with the expression libraries of the prior art.

It has now surprisingly been found that a peptide or protein expression library may be generated in which the specific translation products of the genetic material in the library are directly and covalently attached to the encoding DNA sequence. This then obviates the use of cellular genetic packages with their inherent limitations during the construction and screening of the expression library. This advance allows rapid screening for desired peptides or proteins with cycles of selection, DNA amplification and expression. Whilst DNA amplification may involve self-replication, this may instead conveniently and rapidly be performed using standard amplification techniques, for example polymerase chain reaction (PCR) as will be described in more detail hereinbelow.

Covalent DNA:protein expression libraries of the invention are made possible by the inclusion of a sequence within the genetic material which encodes a protein or portion thereof which binds covalently to its own encoding DNA and which includes, or is overlapping or adjacent to, the coding sequence for the peptide or protein for display. When expressed, the DNA-binding protein and the display peptide or protein form as a single polypeptide, which becomes covalently attached to the encoding DNA. It will be appreciated that such binding will only be possible if the genetic material and its translation product are accessible to one another. Thus, the genetic material should preferably be devoid of sequences which effectively code for peptides or proteins which would interfere with the protein:DNA interaction.

Furthermore, as will become apparent from the discussion below, in certain instances the DNA-binding protein will cleave the DNA to which it becomes attached. Under these circumstances, depending on the construction of the DNA molecules of the library and the placement of the library sequences within them, the DNA binding protein may be covalently attached to a DNA fragment which does not contain the library sequences due to cleavage of the fragment from the remainder of the DNA molecule. However, providing hybridizing conditions are used, the template strand will retain the complementary two coding strand fragments and thus the DNA-binding protein remains associated with its encoding DNA via the intermediary of a covalent DNA:protein bond. Reference to a "direct" attachment as used herein is intended to include this possibility. Furthermore, it is clear in such a case that the DNA-binding protein is attached to a fragment of its encoding DNA. This possibility is however encompassed by the term "specifically associated with the DNA encoding them" as used herein.

Thus viewed from one aspect, the present invention provides a method of producing a peptide or protein expression library which displays a diverse population of peptides or proteins, wherein the peptides or proteins are specifically associated with the DNA encoding them through covalent protein:DNA binding, said method comprising at least the following steps:

1) preparing an amplifiable genetic library of DNA molecules which contain a nucleotide sequence encoding an amino acid sequence which binds specifically to said encoding sequence through covalent protein:DNA binding (binding moiety), a sequence encoding an amino acid sequence for display (display moiety) and at least one site of attachment for the binding moiety and 2) expressing the genetic library thus formed.

Thus, the creation of a multitude of different translation products which attach covalently to their specific encoding genetic material may be realized. This finding has been used for the development of the peptide or protein expression library described herein. This library differs from previous in vivo libraries using cells or unicellular organisms to express the peptides as the peptide or protein for display is presented directly on the genetic material encoding it and not on the surface of a membrane or cell wall.

Furthermore, monovalent or divalent display may generally be achieved and this method allows the expression of extremely high library diversities. Additionally, when PCR amplification of the genetic material which encodes a library member exhibiting desired properties is to be performed, this may be executed in situ on the DNA of that member of the peptide library, as the DNA is freely accessible for binding appropriate primers and does not require prior extraction or elution from the materials used during its selection or non-genetic portions of the peptide or protein library conjugate. This significantly simplifies and quickens the procedure. Furthermore, the harsh treatment e.g. low pH, usually required for elution of the genetic material from target-binding cells or virions prior to amplification is not necessary.

Additionally, in contrast to in vitro expression libraries of the prior art, the covalent linkage between the DNA and the encoded polypeptide means that the displayed peptide or protein will not be released from the DNA by ionic conditions and solvents that would disrupt bacteriophages, DNA binding protein:DNA interactions or ribosomes. Furthermore, covalent attachment allows selection to be carried out at a wider range of temperatures, over longer periods of time and with intermediate freezing steps. Thus selection is much more convenient as well as potentially much more rigorous.

As used herein, the term "binds specifically to said encoding sequence" is intended to indicate that the amino acid sequence whilst it may not uniquely recognize its encoding DNA if isolated and introduced to a series of different DNA sequences, will bind to its own encoding sequence when produced from its encoding DNA by transcription and translation. This specificity may be achieved in a number of ways as described below. As referred to herein, the "encoding" DNA is intended to mean the DNA molecule which when expressed yields a translation product which contains the display protein or peptide and the DNA-binding moiety. The region of DNA to which the DNA-binding moiety binds is however not necessarily within the region coding the display or binding moieties, but is simply present on the same DNA molecule.

Proteins which interact in vitro with the DNA sequence which encodes them are known herein as "cis-acting proteins" (also referred to as cis-proteins) and establish a covalent linkage to their own DNA template. "Pseudo-cis acting proteins" are considered herein to be those proteins which act in cis fashion (ie. bind to their encoding DNA) under appropriate conditions.

A pseudo-cis peptide or protein expression library may be created by the use of a DNA-binding moiety which binds covalently to the DNA encoding it under appropriate conditions. For example this may be achieved by performing the translation step within the confines of a cell or organism in which each cell contains DNA encoding only a single library member.

In this case since the DNA-binding moiety will have only a single recognition and attachment site available (although there may be more than one copy of the DNA), it will bind to its own encoding DNA (pseudo-cis action). This thus provides an operational link between the encoding DNA and the expressed peptide or protein attached through a covalent bond. As used herein, the "attachment site" includes the recognition site with which the DNA-binding moiety associates prior to covalent binding, i.e. this term refers to the nucleotide sequence required to achieve covalent binding of the DNA-binding protein.

Thus the invention provides in a preferred aspect, a method of producing a peptide or protein expression library as defined hereinabove wherein expression of the genetic material is performed in vivo with a single library member, optionally present in more than one copy, expressed per host cell or organism.

Appropriate pseudo-cis proteins are any proteins which recognize specific binding sites (attachment sites) on DNA and which result in a covalent DNA:protein bond. Examples include terminal proteins, replication proteins and other priming proteins. Furthermore, functionally-equivalent fragments, variants or derivatives of known covalent DNA-binding proteins may be used. It will be appreciated that cis-binding proteins described below may also be used in the above-described method.

True cis-acting proteins offer particular advantages for preparing in vitro expression libraries. Examples of cis-acting proteins includes those which are involved in initiating replication. Rolling circle type of replication is commonly used among circular replicons of different origins, for example single-stranded (ss) and double-stranded (ds) DNA phages (Van Mansfield et al. (1984), Adv. Exp. Med. Biol., 179, p 221-230; Baas & Jansz (1988), Cur. Topics Microbiol. Immunol., 136, p 31-70), ssDNA plasmids (Gruss & Ehrlich (1989), Microbiol. Rev., 53, p 231-241; Novick (1989), Ann. Rev. Microbiol., 43, p 537-565), ssDNA plant viruses (Stenger et al. (1991), PNAS, 88, p 8029-8033; Saunders et al. (1991), Nucl. Acids Res., 19, p 2325-2330), ss and ds DNA animal viruses (Berns (1990), Microbiol. Rev., 54, p 316-329; Dasgupta et al. (1992), J. Mol. Biol., 228, p 1-6) and ds DNA bacterial plasmids (Kham, 1997, Microbiol. Molec. Biol. Rev., 61(4), p 445-455). In the systems studied, the initiation proteins possess a nicking-closing and topoisomerase-like activity. The best studied system is that of the ssDNA phage ɸX174, where the A protein nicks the ori site in the viral strand of the replicative form and forms a covalent link to the 5' end of the cleaved strand. The 3' end is thereafter extended by the host polymerase displacing the 5' viral strand and after one round of replication the parental viral strand is religated and the A protein is transferred to the progeny strand to initiate a new round of replication (Baas & Jansz, 1988, supra). The P2 A protein has also been found to cleave the ori site in the coding region of the A gene at a site which is devoid of secondary structure and bind to the 5' end of the cleaved strand (Liu & Haggård-Ljungquist (1994), Nucl. Acids Res., 22, p 5204-5210).

This cis-action has been reported to act in vivo and thus the translation step may be performed in vivo, but with more than a single library member being expressed per cell, before the cell is disrupted to produce the display library. The process which allows the cis-protein to exhibit cis-action despite the presence of other appropriate binding sites on other DNA molecules also contained with the cell or organism is not known although it has been suggested that compartmentalization occurs during translation or that the cis-proteins cannot readily diffuse in the cell.

Thus in a more preferred aspect the present invention provides a method of producing a peptide or protein expression library as defined hereinabove wherein said amino acid sequence which binds specifically to said encoding sequence is derived from a cis-acting protein or a functionally-equivalent fragment, derivative or variant thereof and expression of the genetic material is performed in vivo with at least one library member, optionally present in more than one copy, expressed per host cell or organism.

Appropriate cis-acting proteins which remain cis-acting in vitro include the family of replication proteins including P2A, which are related by sequence (preferably exhibiting 60% sequence identity, more preferably 70, 80 or 90%), organisation and mode of replication; such as equivalent proteins from phage 186 (Sivaprasad et al., 1990, J. Mol. Biol., 213, p 449-463), HP1 (Esposito et al., 1996, Nucl. Acids Res., 24, p 2360-2368) and PSP3 (Bullas et al., 1991, Virology, 185, p 918-921) and functionally-equivalent fragments, derivatives and variants thereof. Cis-acting proteins which are cis-acting in vivo exhibit similar rolling circle replication properties and organisation to P2A. Such proteins include for example the A protein of ɸX174 as mentioned above. Appropriate pseudo-cis proteins are related to P2A, such as terminal proteins, for example from different organisms.

The use of the above libraries allows an increase in the diversity of the library and a reduction in the signal to noise ratio due to the low number of host cells or organisms required relative to known in vivo expression libraries.

Cis-acting proteins have always been assumed to only act in vivo and a corresponding action in vitro has neither been suggested nor observed. Surprisingly, it has however been found that the cis-action is retained even when translation is performed in vitro.

As will be appreciated, numerous advantages flow from this finding. Firstly, the formation of a covalent bond has various advantages as mentioned previously. Furthermore, since the encoded proteins are able to find their encoding DNA despite the presence of neighbouring strands of DNA exhibiting an appropriate binding site, the entire preparation of the library and its screening may be performed in vitro. This radically reduces the time and effort involved in generating and screening and many of the limitations of in vivo libraries are avoided. For example, at least 12 hours may be saved per round of expression, screening and amplification. Since host cells or organisms may be dispensed with entirely, the library may have up to $10^{12}$ different members.

In vitro translation allows the incorporation of many co- and post-translational modifications (which may be made chemically or enzymatically, during or after the translation step), some of which were not previously possible when translation was performed in vivo. For example phosphorylation or sulphation, formation of disulfide bonds, glycosylation or isomerization may be performed. (These steps could also be performed on library members once expressed in vivo and then released.) These reactions may be accomplished in vitro by supplementing the extract with the enzyme responsible for the modification. Non-natural amino acids may also be introduced, by for example chemically charging a t-RNA or by modifying the amino acid on a charged t-RNA.

Thus in an especially preferred aspect, the present invention provides a method of producing a peptide or protein expression library as defined hereinabove wherein said amino acid sequence which binds specifically to said encoding sequence is derived from a cis-acting protein or functionally-equivalent fragment, derivative or variant thereof and expression of the genetic material is performed in vitro.

As used herein, "functionally-equivalent" fragments, derivatives and variants define peptides or proteins related to or derived from a native protein as defined herein (e.g. a cis-acting protein), wherein the amino acid sequence has been modified by single or multiple amino acid substitution, addition and/or deletion which may alternatively or additionally include amino acids which have been chemically modified, e.g. by deglycosylation or glycosylation, but which nevertheless retain the desired functionality, e.g. exhibit cis or pseudo-cis DNA-binding properties. Conveniently, such derivatives or variants may have 80 or 90% sequence identity to the native protein from which they are derived. Functionally-equivalent variants include natural biological variations (e.g. allelic variants or geographical variations within a species) and derivatives prepared using known techniques. For example, functionally-equivalent peptides or proteins may be prepared either by chemical synthesis or in recombinant form using the known techniques of site-directed mutagenesis, random mutagenesis, or enzymatic cleavage and/or ligation of nucleic acids.

It will be appreciated that cis-acting proteins or fragments, variants or derivatives thereof may be used to generate libraries of the invention according to the methods described for pseudo cis-acting proteins, which will be described in more detail below.

Conveniently, the cis-proteins for use in methods of the invention are derived from the phage P2 DNA replication initiation system. The P2 A protein recognizes a defined initiator sequence located within the P2 A gene on the very same DNA molecule which codes for it (cis-action) and specifically nicks one of the strands while forming a covalent bond with one of the free end bases at the nick site (Liu & Haggård-Ljungquist, 1994, supra). Such a protein-DNA complex constitutes a genetic conjugate which can be used for peptide display purposes. The sequence of the P2 A gene has been reported (Liu et al. (1993), J. Mol. Biol., 231, p 361-374).

It is known that the P2 A protein can tolerate amino acid alterations (see for example Liu et al., 1993, supra) and thus display peptides or proteins may be introduced without loss of function. The property of cis-action of A allows peptide or protein library constructions in vitro by subjecting a library of DNA templates (with sequences encoding various hybrid A peptides or proteins for display, an appropriate promoter for transcribing the A gene and the site to which P2A binds) to a cell-free coupled transcription/translation step. This results in hybrid A peptides or proteins binding covalently to their own template DNA.

The hybrid A:DNA conjugates constitute an in vitro peptide or protein library displaying the different hybrid A peptides or proteins which can be subjected to panning against a target or tested for a desired activity. The specific hybrid A:DNA conjugates which bind to the target or exhibit a desired property may be recovered, where necessary, and the genetic material may then be amplified, by for example PCR, and subjected to a coupled transcription/translation step in a cell-free extract. This cycle may then be repeated as desired to obtain an individual hybrid A:DNA clone. This may be monitored by DNA sequencing until an appropriate number of DNA sequences are obtained. Appropriate techniques for screening are described in more detail below.

As used herein in reference to the peptide or protein expression library which displays a diverse population of peptides or proteins, the term "peptide or protein" is intended to cover an amino acid sequence which contains at least a display sequence (the display moiety) (which may be contained within, overlap with, or be distinct from the sequence which binds to the encoding DNA), which is varied in different members of the library and which may be selected through appropriate selection procedures. Each expression library member also contains as part of the expressed polypeptide, an invariant sequence (which may be part or all of the sequence) which is responsible for attachment of the peptide or protein resulting from expression to the encoding DNA (the binding moiety). Necessarily, both the binding and display moieties are expressed on a single peptide or protein.

When the display moiety is larger than a peptide (and referred to herein as the display protein), it is likely that various amino acids of the protein will be invariant, such as when a protein is used as a scaffold, and that the library members will differ only in certain regions of the display protein.

The DNA sequences encoding the peptides or proteins for expression in libraries of the invention, containing sequences encoding the display and binding moieties and at least one site of attachment for the binding moiety, wherein the nucleic acid molecules include molecules with degenerate and/or functionally-equivalent sequences, form a further aspect of the invention. Functionally-equivalent nucleic acid molecules include fragments, derivatives and variants, for example substantially homologous and hybridizing sequences which encode peptides or proteins as defined herein having the required functionality, e.g. cis-binding action.

By "substantially homologous" is meant sequences displaying at least 60%, preferably at least 70 or 80% sequence homology. Hybridizing sequences included within the scope of the invention are those binding under non-stringent conditions (6×SSC/50% formamide at room temperature) and washed under conditions of low stringency (2×SSC, room temperature, more preferably 2×SSC, 42° C. or conditions of higher stringency e.g. 2×SSC, 65° C. (where SSC=0.15M NaCl, 0.015M sodium citrate, pH 7.2), as well as those which, but for the degeneracy of the code would hybridize under the above-mentioned conditions.

It will be appreciated that by the production of a library of DNA sequences (with associated encoded proteins or peptides), the present invention also provides a DNA display library. Thus a bifunctional library is provided for selection of members based on their display peptide/protein or DNA moieties.

The invention is conveniently performed using the P2 A protein or a functionally-equivalent fragment, derivative or variant thereof as the binding moiety. The relevant nucleotide sequence for binding the DNA-binding moiety must also be provided at a suitable site, although this may be moved from its naturally-occurring position. In the case of for example P2A, at least the sequence TCGGA, for example in the sequence GCGCCTCGGAGTCCTGTCAA, should be included in the DNA encoding the peptides or proteins of the expression library or a functionally-equivalent fragment, derivative or variant thereof which is recognized by the DNA-binding moiety and forms a covalent bond therewith. Conveniently the sequence encoding the display moiety is inserted in, overlaps with, or is adjacent to the sequence encoding the N-terminal of the P2 A protein.

The DNA molecules used to generate the library may be provided with means for both amplification and transcription. Suitable DNA molecules with means for amplification include double-stranded DNA with a replication origin, for example self-replicating plasmids which may thus replicate in vitro in for example cell-free extracts or in vivo if present in host cells. When DNA is unable to self-replicate, this may in appropriate instances be overcome by the inclusion of a replication origin. For example, certain proteins described herein, such as P2A, bind to their own replication origin. If the protein is not released from the origin (such as when mutants described herein are used), replication of the DNA molecule containing the DNA-binding moiety gene is inhibited. In these cases a second replication origin may be included. Conveniently, nucleic acid molecules for generating the library are in the form of vectors, plasmids or linear DNA.

Alternatively, the DNA may be amplified through technical intervention, for example by providing the DNA with appropriate sites for binding primers for a amplification reaction, for example PCR, allowing amplification in vitro. Clearly such sites would in most cases inherently be present in any DNA molecule such that the appropriate choice of primers would facilitate amplification.

Means for transcription include the provision of a promoter sequence. If a wild-type gene, or a degenerate sequence or functionally-equivalent fragment, derivative or variant thereof is used, the promoter may be constitutively present. If not, an inducible or non-inducible promoter may be included. In cases where the product of translation would inhibit transcription (such as when a mutant P2A is used as described herein) it is advisable to use an inducible promoter, which may be activated only during the transcription/translation step. Alternatively in such a case, a non-inducible promoter may be used if this effectively acts in an inducible manner, e.g. by very low transcription under appropriate conditions (e.g. T7 in bacterial hosts containing a regulated T7 polymerase gene or by supply of a promoter at an appropriate time, e.g. by viral infection). If however a non-inducible promoter is used, if, during the course of library screening, translation is to be performed in a bacterial host, an inducible polymerase gene must be present in the bacterium or introduced by infection.

Examples of appropriate inducible promoters include AraB, lambda promoter (in cells expressing a temperature sensitive repressor, such as N4830-1), or a TAC or LAC promoter combined with an efficient LAC O sequence. Suitable non-inducible promoters include the T7 promoter, or SP6 or T3 promoters. The promoter should be upstream of the polypeptide to be expressed, but this may be achieved if the promoter is downstream by circularization of linear DNA.

DNA molecules for use in the preparation of the library must also necessarily contain diverse display peptide or protein encoding sequences to obtain a library of different peptides or proteins for display. Such different sequences may be introduced by for example randomization as described in the literature using randomized primer sequences in PCR (Schmidt and Skerra (1993), Protein Engineering, 6, p 109-122) as described in more detail below. Randomized primer sequences may be produced using standard chemical synthesis with commercial DNA synthesizers or may be purchased commercially. Alternatively, especially where variation is to be made in non-contiguous amino acids, megaprimers may be produced and varied by mutagenesis.

The DNA molecules with the features necessary for the generation of a library form a further aspect of the invention.

Expression of the genetic material of the library may be performed as described in more detail below.

Viewed from a further aspect, the invention provides an in vitro peptide or protein expression library which displays a diverse population of peptides or proteins, wherein the peptides or proteins are specifically associated with the DNA encoding them through covalent protein:DNA binding, and wherein said encoding sequence is carried on a DNA molecule which contains a sequence encoding an amino acid sequence which binds specifically to said encoding sequence (binding moiety), a sequence encoding an amino acid sequence for display (display moiety), and at least one site of attachment for the binding moiety.

As will be clear from the above, the invention provides many different types of libraries and methods for their generation. Although methods for the preparation of such libraries would be within the scope of the skilled addressee, the following is provided to illustrate some types of libraries and how these might be created, with particular reference to the use of the gene encoding P2A as an example of a cis-acting protein.

A library may be created in which the peptides or proteins for display exhibit random, pseudo-random, partially random or scattered variation and all or part of the genetic material encoding members of the library may be synthesized chemically or derived from genomic/coding sequences from various organisms. The varied regions may be contiguous or non-contiguous. Combinatorial libraries (wherein the varied regions are contiguous) generally consist of less than 20 amino acids due to the possible number of permutations. It is therefore appropriate to use non-contiguous regions of variation for longer stretches of amino acids. Thus for example, in a display peptide of 40 residues, permutations of only 13 of these amino acids might be generated. This has the advantage of reducing the total number of permutations (library members) relative to a library in which all positions were varied. The use of sequences in which certain residues are invariant provides a scaffold (invariant) structure with certain regions contained within, or supported by the scaffold, which are varied.

These scaffold structures may exist inherently in proteins in which libraries could be used to isolate variants of the proteins exhibiting desired properties, based on variation at selected residues. Thus for example, the specificity or thermal stability of an enzyme could be varied if the original enzyme was used as a scaffold. Alternatively, scaffold sequences may be introduced adjacent to or within the DNA-binding moiety for presentation of a non-contiguous display peptide or protein. Scaffold sequences may be located at one or more sites anywhere within the sequence of the peptide or protein which attaches to its encoding DNA providing the scaffold sequence(s) does not interfere with the covalent attachment of the encoded peptide or protein to its DNA.

As mentioned previously, genetic material encoding the different library members may be generated through the use of primers in which a portion of the primer is varied (to generate a primer array) to produce the permutations described above. Up to $10^{12}$-$10^{14}$ library members may be created in this way. In the case of encoded products (such as P2A and its functionally-equivalent fragments, derivatives or variants thereof) which bind to their encoding DNA via the coding strand, to allow transcription of the template strand and binding of P2A to the coding strand, it is necessary for the ultimate products resulting from generation and amplification (if the latter is performed) to be both template and coding strands. This may be achieved by the use of, for example, template strand primers containing library sequences (i.e., a pool of varied primers), additionally containing a template strand primer binding site to permit further amplification if this is required. This site may furthermore be used as a unique identifier for selection (and amplification) post-screening. Once a set of template strands have been generated which include the library sequences, a suitable primer which binds to the template strand may be used to produce coding strands containing the library sequences.

Generation of the nucleic acid molecules for the preparation of the library and/or their amplification may readily be performed using a combination of these primers simultaneously or consecutively. If amplification is to be performed at the same time as generating the library, a single primer may be used to perform a series of linear amplifications followed by the use of the second primer, or both reactions may be performed together. Primers may be composed of nucleotide bases which may be derivatized (e.g. with an immobilization moiety), or alternative appropriate constituents, such as derived from PNA, or combinations thereof.

Nucleic acid molecules encoding for different library members or the variable parts thereof may alternatively be generated by mutation or cloning, optionally in combination with amplification techniques. Thus for example, an initial library may be created by cloning and used as an initial template which may be further varied by using a primer array with library sequences and/or by random mutagenesis.

Of primary importance in nucleic acid molecules for preparing expression libraries of the invention is the region encoding the DNA-binding moiety. As mentioned previously, this includes any DNA-binding protein or functionally-equivalent fragment, derivative or variant thereof which forms a covalent bond with its encoding genetic material to form an operative link. Depending on whether the translation step is to be performed in vitro or in vivo with a single or multiple library members per host cell or organism, the DNA-binding moiety may act in cis or pseudo-cis fashion. An example of a cis-acting DNA-binding moiety which is appropriate for use in the invention is the P2A protein or its functionally-equivalent fragments, derivatives or variants thereof.

An appropriate fragment comprising at least the region of the DNA-binding protein which is necessary to achieve covalent binding to the DNA must be present in the nucleic acid molecules used to form the library. For example, in the case of P2A, the gene encoding the protein or a degenerate sequence or functionally-equivalent fragment, variant or derivative thereof with appropriate DNA-binding properties should be present. This gene may be varied by the addition or deletion of sections of the gene if the resultant expressed peptide or protein retains its functional activity, ie. still results in a covalent bond to the DNA. For example, the peptide/protein binding site on the DNA (attachment site) may be moved or an additional binding site introduced (for example, if the wild type binding site is non-functional due to variation e.g. by mutation). This is particularly important to ensure that the display peptide or protein remains attached to the DNA which encodes it when the DNA-binding moiety which is used additionally results in nicking of the DNA.

Furthermore, the region encoding the display peptide or protein (display moiety) may be inserted within, lie adjacent to or fall outside the region encoding the DNA-binding moiety, provided that the display moiety once expressed is covalently attached to the DNA-binding moiety, i.e. is part of the same expressed peptide or protein. This may require movement of the termination codon to downstream of the region encoding the display moiety. As with the positioning of the protein-binding site on the DNA, it should be ensured by appropriate positioning of the region encoding the display moiety that the display moiety remains attached to the DNA which encodes it, especially when nicking of the DNA coding strand is involved. This may be achieved in a number of different ways.

Nicking occurs on the coding strand and the DNA-binding peptide or protein (linked to the display peptide or protein) is covalently attached to the 5' end created during the nicking process. Thus it should be ensured that the genetic material encoding the display moiety is carried on the part of the coding strand covalently attached to the expressed peptide or protein or remains associated with it. If DNA is retained in double-stranded form following translation and during selection, then the template strand will ensure that both coding strands are associated with the DNA-binding moiety.

Alternatively, circular DNA may be used for translation which will result, after nicking (under non-hybridizing conditions), in a linear coding strand comprising the entire coding strand prior to nicking. Alternatively if neither circular DNA is used nor hybridizing conditions, the protein attachment site and the site of the library sequences should be chosen such that the DNA-binding moiety covalently attaches to the part of the coding strand encoding the display moiety. This may be achieved by insertion of the display moiety encoding region at the carboxyl encoding terminal side of the attachment site (wherein the latter may also be displaced from its natural position). This is most readily achieved by insertion downstream of the naturally occurring attachment site, ie. at the carboxyl encoding end. However, the region encoding the display moiety may be introduced at the amino end if the attachment site is also shifted upstream.

If necessary, the attachment site may be shifted to precede the entire coding region. When the region encoding the display moiety is to be inserted at the amino end, to ensure transcription, if the library sequences are introduced by primers, megaprimers should be employed comprising additionally at least an appropriate promoter and initiation codon preceding the library sequences.

Library sequences may be inserted within the coding region, rather than at the amino or carboxyl end, by for example amplification of circularized DNA using primers which hybridize to the coding sequence but additionally comprise library sequences in a non-hybridizing portion. After extension using such a primer, an appropriate primer may be selected to produce a hybridizing strand in which the terminal strands of the double stranded extension product (after hybridization) are blunt or after digestion with an appropriate restriction endonuclease exhibit overhang such that ligation may be performed to produce DNA molecules with internally inserted library sequences.

If proteins are to be displayed, e.g. as a scaffold, then it will be appreciated that the display protein should be inserted into the coding sequence or relevant site and subsequently varied at specific residues or regions to produce the library.

Additionally, the positioning of the region encoding the display moiety should be determined by the tolerance of the encoded peptide or protein, particularly the DNA-binding moiety, to insertions or replacements at that site.

Nucleic acid molecules of the invention may additionally comprise further features such as antibiotic resistance markers. For example, the gene for β-lactamase may be included when steps of amplification and/or translation/transcription and/or screening and/or isolation might involve transformation, to allow identification and selection (by their antibiotic resistance) of appropriate transformants.

The molecules may contain alternative markers or reporter molecules (for example radiolabelled nucleotides or one partner of a binding pair such as streptavidin:biotin) such that the presence or identity of said nucleic acid molecules may be ascertained. The marker or reporter molecules may also be used as a tool for immobilization and/or purification of the nucleic acid molecules, for example in the case of a biotin marker, a streptavidin-bearing column may be used to collect the molecules. Additionally, nucleic acid molecules which encode the library may include non-natural nucleotides or methylated bases, especially in the flanking sequences, to stabilize the DNA in cell lysates and/or during selection.

For convenience, any of the primers used in the methods described above may also have an immobilization moiety attached, such as biotin, to allow their extension products (the genetic material encoding the library) to be readily be isolated for later steps. Furthermore, where appropriate, the primers may be provided with features to be incorporated into the resultant nucleic acid molecules, e.g. promoter sequences, termination sequences, genes required to confer antibiotic resistance.

Once nucleic acid molecules encoding the library have been created, the library may be generated by the steps of (i) amplification of the genetic material, (ii) transcription and (iii) translation, wherein the latter two steps will usually be coupled. Depending on whether a cis or pseudo-cis DNA-binding protein function is employed, these steps may be performed in vitro or in vivo. When cis-binding proteins are used each step may be performed either in vitro or in vivo. When pseudo cis-binding proteins are used, amplification may be performed in vitro or in vivo, but transcription and translation must be performed in vivo.

Amplification may be performed in vitro during the generation of the genetic material for the library if for example primers and PCR are used to generate the molecules. Alternatively or additionally, the nucleic acid molecules may be amplified by conventional in vitro amplification methods such as PCR, NASBA (also known as 3SR) (see Malek et al. (1994), Methods Mol. Biol., 28, p 253-260; Gebinoga & Oehlenschlager (1996), Eur. J. Biochem., 235, p 256-261; and Ehricht et al. (1997), Eur. J. Biochem., 243, p 358-364) or linear amplification. Alternatively replication may be performed in vitro using cell-free extracts (see for example Kool, 1996, Ann. Rev. Biophys. Biomol. Struct. USA, 25, p 1-28) or in vivo after insertion of the nucleic acid molecules into host cells or organisms, for example by transfection.

If replication is performed in vitro the cell-free extract should be chosen appropriately, for example it should contain dNTPs. Circularization may be performed prior to transfection or replication where necessary. Furthermore, as mentioned below, to avoid detachment of the DNA-binding protein which occurs during replication, a non-detachable mutant may be required. The nucleic acid molecules may already exist in host cells or organisms if their generation was by mutation.

The generation of the library expressing the display peptide may be performed in vivo by growing up transformed cells or organisms. Appropriate organisms for this purpose include bacteria (such as *E. coli*), viruses, bacteriophages and cells such as yeast, or prokaryotic, eukaryotic cells or archaebacteria may be used. To release the expression library, the cells or organisms should then be lysed to release the protein/peptide:DNA expression units and/or the genetic material encoding the library and purified (e.g. plasmid or minichromosome) prior to transcription/translation. However as used herein, the term "library" is intended to encompass a collection of library members still contained within their host cells or organisms when created in vivo as well as library members after release, if produced in vivo, or if created in vitro.

In vitro, coupled transcription/translation may be performed in cell-free extracts. This may conveniently be performed in cell-free extracts from prokaryotes or eukaryotes, for example of *E. coli* (Nevin & Pratt (1991), FEBS, 291, p 259-263). Prokaryotic (e.g. *E. coli*, S-30 or S-135) and eukaryotic (e.g. wheat germ or reticulocyte) cell-free extracts are available commercially (Amersham/Promega). Depending on the construct of the DNA molecules and whether a nicking protein is encoded, it may be necessary to circularize the DNA before translation to ensure that the display moiety remains associated with its encoding DNA.

Whether performed in vivo or in vitro, where an inducible promoter has been used, the transcription process should be induced.

It has been found that the binding of certain DNA-binding proteins (e.g. P2A) may be improved in vitro, for example by altering the properties of the attachment site. Alternatively, specific cofactors (e.g. specific host proteins) may be required to enhance the binding and activity of the DNA-binding proteins. Preferably, the attachment site should be single-stranded. This can be accomplished in a number of different ways, for example when using double stranded DNA a loop or opening may be introduced at the attachment site. A mis-match oligonucleotide may be included during the translation reaction which hybridizes to the coding strand on both sides adjacent to the attachment site. In the region containing the attachment site on the coding strand, the corresponding portion of the mis-match oligonucleotide is unable to hybridize thus making the coding strand effectively single stranded over this region. The use of a mis-match primer forms a preferred aspect of the invention.

This mis-match region may extend for the length of the attachment region or may extend beyond this region, for example may be mis-matched over a region of 10 nucleotides. For example in the case of the P2A attachment site (TCGGA, present in the sequence 5'-AGCGGCATCGCCGCGC-CTCGGAGTCCTGTC-3'), a mis-match oligonucleotide containing a sequence such as 3'-TCGCCGTAGCGGCG-TAAGTATTCTAGGACAG-5' may be used in which the region of mis-match is underlined.

Alternatively, appropriate primers may be used in generating the nucleic acid material encoding the library and/or amplification thereof to introduce a single-stranded region at the attachment site. This may be performed by for example using a primer which has a mis-match region to the attachment site. If the attachment site is within the coding region of the DNA-binding moiety then the sequence of the mis-match should be selected so as not to affect the amino acid sequence encoded by the DNA and should hence be a silent variation, ie. variation of the codon in the third position, but encoding the same amino acid. It has been found by the present inventors that improved attachment was observed when a mis-match was present in the template strand corresponding to the attachment site on the coding strand.

Alternatively if the attachment site is at the end of the coding region and a mismatch primer is used, appropriate primers may be selected after the screening step such that during amplification the attachment site is restored.

Alternatively, if the attachment site is formed at the end of the DNA, the double stranded DNA in this region may be made single stranded by digestion with a restriction endonuclease that leaves a 5' extension containing all or part of the attachment site. For example, the enzyme HgaI leaves a 5 base 5' overhang 5 nucleotides from the HgaI recognition site. If this region is too small then a larger region may be made single stranded by the incorporation of non-natural bases in a primer for amplification (e.g. deoxyuridines) followed by the use of DNA repair enzymes such as uracil DNA glycosylase or T4 endonuclease to excise specific nucleotides leaving a single stranded region (Watson & Bennet (1997), BioTechniques, 23, p 858-864).

When the invention is performed using certain cis-binding proteins such as P2A, or their functionally-equivalent fragments, derivatives or variants, whilst the DNA-binding moiety will associate covalently with the DNA encoding it, this represents a kinetic intermediate and if replication is occurring, the peptide or protein will religate the coding strand and detach from this strand transferring to a further coding sequence with an intact attachment site. Replication may be avoided in vitro, but this transfer represents a potential problem in cases in which translation is conducted in vivo.

To avoid this, a mutant may be used which does not detach. The use of a modified binding moiety which remains covalently attached to its encoding DNA in methods of the invention forms a preferred aspect of the invention. In the case of P2A for example, Y450F which comprises a substitution of the tyrosine at amino acid position 450 of the A-protein with phenylalanine may be used. It should however be noted that when the translation reaction is performed in vitro, providing replication does not occur (e.g. by ensuring no dNTPs are present), wild-type protein will remain associated with the DNA encoding it allowing screening to be performed.

A library generated as described herein may be used for any of the applications for which conventional in vivo or in vitro display libraries of the art are used. Such uses are well documented in the literature. For example, the library of the invention may be used to identify a peptide or protein which binds specifically to a target molecule.

It is known in the art that peptides of different size may be arranged in an appropriate tertiary structure to produce a domain with particular steric and charge characteristics. Such a domain may, by virtue of its specific tertiary arrangement, specifically recognize or bind to a particular target molecule. Examples of such peptides include, but are not limited to binding regions of proteins and the variable binding regions of antibodies. Even small peptides without defined tertiary structure may also have specific target binding properties. The peptides for display by the library of the invention may thus be small peptides, for example up to 40 amino acid residues, e.g. 5 to 30, preferably 7 to 20 and most preferably 10 to 15 amino acid residues, which do not have a fixed tertiary structure, or may be larger peptides which form a fixed tertiary structure.

Alternatively, the library may express display proteins (forming part of the polypeptide containing the DNA-binding moiety) in which only certain residues are varied in the different library members. For example, a protein with defined specificity, such as an antibody or receptor may form the basis of a library in which several, for example 5 to 30, preferably 7 to 20 amino acid positions are varied in the library and display proteins exhibiting altered specificity may be selected.

Target molecules may include small chemical compounds, for example heterocycles or pharmaceutical compounds, polypeptides, proteins, polynucleotides or any entity having distinctive surface characteristics which may be specifically recognized. Thus, for example, specific target-binding peptides or proteins may be identified which would have utility in diagnostic assays, for example in clinical procedures to assess the levels of biological or non-biological molecules in the human body or samples, extracts or material derived therefrom, or in assays which ascertain the levels of biological or non-biological materials in other non-biologically derived materials.

Libraries according to the invention also have utility in screening protocols for identifying compounds with appropriate biochemical, biological or structural properties, for example to identify peptides or proteins which have certain biochemical activity in a defined assay. By this method, peptides or proteins with enzymatic, inhibitory or stimulating properties may be identified which may have utility in for example the pharmaceutical field. For example, enzymatic activities may be screened by monitoring for example increased or decreased bioactivity such as chemifluorescence, nuclease activity, phosphotransferase activity, inhibition etc. If scaffold polypeptides are used with known activity, variants with altered properties or activity may be selected from the library.

Such peptides or proteins once identified from the library may be used for the preparation of compounds with the particular activity for example, inhibitors, activators, or catalysts of certain reactions or interactions.

In general, peptides or proteins of interest are identified from the library according to the following protocol including the steps of (i) screening, (ii) isolation and/or purification, (iii) evolution, (iv) amplification, (v) preparation of a library for re-screening (including transcription and translation) (vi) re-screening (and thereafter following steps (ii) to (vi) as many times as appropriate) and (vii) isolation of the genetic material of interest. Steps (ii) and/or (iii) and/or (iv) may however be waived as appropriate.

Regardless of whether cis-acting or pseudo cis-acting proteins are used, the screening and isolation steps must be performed in vitro. If cis-acting binding proteins or their functionally-equivalent fragments, derivatives or variants are employed, the remaining steps may be performed in vitro or in vivo. However if pseudo cis-acting proteins or their functionally-equivalent fragments, derivatives or variants are used, at least part of step (v), namely transcription and translation, must be performed in vivo.

Screening, which must be performed in vitro involves the use of an appropriate assay, such as affinity binding, phase partitioning or an enzymatic assay to identify display peptides or proteins of interest as described hereinbelow in more detail. Phase-partitioning (see for example Garg et al., 1994, Biotech, Appl. Biochem., 20, p 119-215) has particular applications for identifying display peptides/proteins which partition to the organic phase (e.g. Triton X-114) as a result of variation within the library. This method is of more general applicability if the organic phase, e.g. detergent is modified to carry an appropriate binding partner for the target display peptide or protein, e.g. an antibody or antigen.

Identification of altered enzymatic properties relies on altered physical properties, e.g. binding to a substrate or exposure of a previously inaccessible site, e.g. by protease activity or phosphorylation.

Binding of the display peptide or protein to an appropriate binding partner may be identified by any appropriate means, by for example affinity binding and elution or evidence of the enzymatic activity, e.g. production of the reaction product. Thus, libraries of the invention may be used to identify binding partners in which the expressed peptide or protein is one of the binding partners. In this way libraries of the invention can provide entirely in vitro alternatives to techniques such as the two-hybrid system. In such a system, two hybrid molecules are created in which each molecule carries one of a binding pair (such as an enzyme and substrate). When these binding partners bind, the other functional parts of the fusion proteins are brought together. By appropriate selection of these functional moieties of the fusion proteins, a detectable interaction may be identified.

This type of system is described for example by Field & Song (1989, Nature, 340, p 245-246) in which the fusion proteins contain different parts of GAL4 from *Saccharomyces cervisiae*, which components when brought together by binding of the binding partners expressed on the fusion proteins, reconstitute GAL4 such that its transcriptional activation activity may be observed. This thus signifies binding between the binding partners of the fusion proteins. Gyuris et al., 1993, Cell, 75, p 791-803, similarly describes the complementation of the components of a transcription activator. Furthermore, complementation using β-galactosidase deletion mutants has been described by Rossi et al (1997, Proc. Natl. Acad. Sci. USA, 94, p 8405-8410). Complementation may also be achieved in which the second fusion protein is a more complex entity but which has the features described above, ie. one partner of the binding pair and a functional moiety which interacts with a functional moiety on the first fusion protein. An example of this is provided by Krebber et al. (1997, J. Mol. Biol., 268, p 607-618) in which non-infectious phage are made infectious by binding of a fusion protein through appropriate binding partners. Aronheim et al. (1997, Mol. Cell. Biol., 17, p 3094-3102) describe a system in which the second fusion protein equivalent has a binding partner which is nucleic acid in nature and the functional moiety is a protein present in the plasma membrane to which the binding partner is bound.

Thus the library of the invention may express a fusion protein with one moiety responsible for a binding interaction (all or part of the display peptide or protein) and a second moiety involved in complementation. A second fusion protein (or appropriate entity) which carries the binding partner and the component required for complementation may form part of the library or may be added to the library. The binding partner of one or both of the fusion proteins may be varied in the library.

Depending on the construct of the nucleic acid molecules of the invention, as mentioned above, it may be necessary to perform the screening under hybridizing conditions.

The library may be modified prior to screening, for example by modulating the folding of the displayed peptide or protein by adding enzymes such as chaperones (for example, hsp70) or folding modifiers such as protein disulphide isomerase, oxidizing agents, or enzymes that alter the oxidizing activity of the bacterial cytoplasm or of translation extracts. Furthermore, both homo-oligomeric and hetero-oligomeric proteins may be screened. For example, the signal recognition particle receptor (SR) is a heterodimer of subunits called SR-alpha and SR-beta and a library expressing variants of only one of the subunits may be expressed. The variants may then be assayed for a desired property independent of the other subunit, or for a property dependent on prior heterodimerization with the other subunit.

A classic example of heterodimerization is provided by the heavy and light chains of an antibody. In this case for example only one chain might be present in the library and the other chain could be supplied during assay. In addition to a polypeptide, metal, porphyrins, cofactors, DNA, RNA and other molecules may all be added at the screening stage to alter the properties of the displayed peptide or protein.

Following screening, display peptides or proteins of interest must be removed from the pool of the library (isolation) and optionally purified. In certain cases this will have been achieved during screening, for example in the use of affinity columns.

Evolution of the selected DNA molecules may be performed to generate further variations in the library which may exhibit the desired properties to a greater extent. This has been performed in the prior art to evolve a fucosidase from a galactosidase (see Zhang et al. (1997), PNAS USA, 94, p 4504-4509) or to alter a specific enzymatic function (see Crameri et al. (1997), Nature Biotechnology, 15, p 436-438; You & Arnold (1996), Protein Eng., 9, p 77-83).

Evolution may be performed by the introduction of additional novel mutations at random locations chemically using any one of a number of procedures known in the art; genetically using mutator strains of bacteria (Degnen & Cox (1974), J. Bact., 117, p 477-487), bacterial strains that introduce amino acid substitutions using suppressor tRNAs (Markiewicz et al (1994), J. Mol. Biol., 240, p 421-433), by mutagenic PCR techniques such as regional codon randomization (Cormack & Struhl (1993), Science, 262, p 244-248) or using one of the standard methods to lower the fidelity of the polymerase used in a PCR reaction or reverse transcriptase in NASBA. Mis-match primers or megaprimer libraries may be used to introduce substitutions at defined locations. The selected library members containing different independent variations can also be recombined using DNA shuffling (Stemmer (1994), Nature, 370, p 389-391) or by more traditional cloning methods.

Following isolation, or evolution if this is performed, the selected library members or evolved library members are amplified (where necessary) and a library prepared for re-screening using any of the procedures described above for the generation of the library. As a consequence of a peptide or protein being bound to the genetic material of the library, to obtain the genetic material in a suitable form for subsequent steps, e.g. transformation, it may be necessary to remove the coding region into a different DNA molecule, such as a vector. Re-screening may then be performed as many times as is appropriate to stabilize the selected population, optionally increasing the stringency of the screening or introducing further variation (e.g. in vitro evolution).

Once screening is complete, the genetic material encoding the selected peptide or protein may be isolated, for example by purification of the plasmid or minichromosome. Optionally the selected library members may be amplified prior to isolation, for example by transformation and culture or by PCR.

From the above it will be clear that various methods may be used to generate and screen the library of the invention. However, the following schemes are preferred. When using cis-binding proteins or their functionally-equivalent fragments, derivatives or variants, to allow the most rapid and efficient protocol (as described previously) all of the steps should be performed in vitro. Since in such cases no living organisms are required, it will be appreciated that the entire procedure is amenable to automation. Furthermore, it is not necessary to use conditions and procedures which are selected to ensure the viability of the organisms.

Preferably, the genetic constructs used to create the expression library are constructed using primers (with library sequences) which anneal to and insert the library sequences at the carboxyl end of the DNA-binding moiety. This avoids the requirement for hybridizing conditions during translation or circularization before translation when using DNA-binding moieties which behave in a similar manner to P2A.

It is furthermore preferred, when using DNA-binding proteins or functionally-equivalent fragments, variants or derivatives thereof which tend to detach from the DNA by which they are encoded, to mutate the DNA-binding protein, e.g. Y450F as described herein, so that the protein or its fragment, variant or derivative will bind to this but not be detached (thus maintaining the operational link between the DNA and its encoded product). Additionally a further ori site may be required to allow replication. The construct should furthermore contain inducible promoters.

Preferably the DNA-binding moiety is derived from the P2A protein or a functionally-equivalent fragment, variant or derivative thereof. During translation, the use of a mis-match oligonucleotide may be desirable. The presence of at least one antibiotic resistance marker is also preferred for ultimate transformation of the selected nucleic acid sequence into host cells once isolated.

When pseudo cis-binding proteins or their functionally-equivalent fragments, derivatives or variants are employed when generating the library, amplification of the genetic material is preferably performed in vitro by appropriate techniques such as PCR. The constructs preferred are those in which the library sequences appear at the carboxyl end of the region encoding the DNA-binding moiety, to avoid the use of megaprimers and problems in the event that nicking of the DNA strand occurs. The presence of genes encoding for antibiotic resistance markers and an inducible promoter is also preferred. During screening, it is preferred that amplification is also conducted in vitro.

Thus viewed from a further aspect the invention provides a method of identifying and/or purifying a library member exhibiting desired properties from a peptide or protein expression library as defined hereinbefore, said method comprising at least the steps of a) screening a library of the invention and b) selecting and isolating the relevant library member. The method may be extended to isolating the peptide or protein exhibiting the desired property or the DNA encoding it by the additional step of isolating the peptide, protein or encoding DNA from the isolated library member.

In instances in which the desired property is the ability to bind to a target, target molecules, preferably in purified form, may be used to select a specific target-binding peptide- or protein-bearing genetic conjugate from the library in a number of different ways. Conveniently, the target may be attached to a solid support and used as an affinity matrix. Numerous solid supports and methods for the attachment of molecules directly or indirectly, covalently or non-covalently (e.g. by a streptavidin-biotin or IgG-protein A coupling) are well known in the art and widely described in the literature.

Thus for example, supports in the form of microtitre wells, tubes, dipsticks, particles, fibres or capillaries may be used. Advantageously, the support may comprise magnetic particles e.g. the superparamagnetic bead produced by Dynal AS (Oslo, Norway and sold under the trademark DYNA-BEADS).

For selection, the expression library may be contacted with the target attached to a solid support. The support may be washed to remove members of the library which do not bind to the target or extracted from the expression library as appropriate for the support being used. Selected peptide/protein:DNA conjugates may then be released from the solid support, if necessary, through disruption of the binding between the target molecules and solid support or target molecules and peptide/protein:DNA conjugates for subsequent amplification or isolation of the genetic material. Alternatively, amplification may be performed in situ without disruption of the target to peptide/protein:DNA conjugate bond or release of the genetic material from the conjugate.

The target molecule may also be used as a free agent in the absence of a support. Selection may then be performed by removal of non-bound conjugates, for example by using antibodies directed to a region of the expressed peptide or protein which is present on all members of the library and which is only accessible when not bound to target molecules. Target molecules may alternatively be provided with a means for immobilization such that this may be used to remove the target and bound peptide/protein:DNA conjugates after mixing of the target and library. Such means for immobilization may for example constitute one partner of a coupling pair e.g streptavidin-biotin, attached to the target molecule and the other partner attached to a support to be used for retrieval.

Thus viewed from a yet further aspect, the invention provides a method of identifying a specific target-binding peptide or protein, said method comprising at least the steps of a) screening a library of the invention with target molecules and b) selecting and isolating a library member binding to said target molecule, and c) isolating the peptide or protein which binds specifically to said target molecule. A method of isolating DNA encoding a specific target-binding peptide or protein is also provided in which after step b) above, the DNA expressing the peptide or protein which binds specifically to said target molecule is isolated.

More than one cycle of screening and selection may be necessary to obtain a target-binding peptide or protein of the desired specificity.

Similarly, the library may be screened to identify a protein or peptide with particular functional attributes, e.g enzymatic activity.

A selected peptide or protein attached to its encoding DNA may be isolated by separation from the genetic material, may be synthesized by transcription and translation of the genetic material which may be amplified, or may be synthesized chemically after sequencing of the appropriate DNA sequence encoding it or direct sequencing of the peptide or protein. Chemical synthesis of the peptide or protein may be performed by methods well known in the art involving cyclic sets of reactions of selective deprotection of the functional groups of a terminal amino acid and coupling of selectively protected amino acid residues, followed finally by complete deprotection of all functional groups. Synthesis may be performed in solution or on a solid support using suitable solid phases known in the art.

Preferably, if the affinity of the selected peptide or protein for the target molecule or activity of the peptide or protein is not significantly affected, only the display moiety of the expressed peptide or protein may be synthesized. Optionally it may be necessary or preferable to produce the peptide or protein as it appears in the polypeptide containing the DNA-binding moiety by generation of some or all of the sequence of the DNA-binding moiety and/or other regions of the expressed peptide or protein. This is especially true when a scaffold library has been produced.

Appropriate target-binding peptide/protein:DNA conjugates may be provided with a reporter molecule for use in qualitative or quantitative assays for determining the presence or absence of target molecules.

Thus, viewed from a yet still further aspect, the invention provides a method of assaying for the presence of a target molecule in a sample, said method comprising (a) contacting said sample (e.g. of biological, biologically-derived or non-biological material) with a molecular probe comprising (i) a peptide or protein target-binding moiety capable of selectively binding to said target molecule, with attached encoding DNA, the DNA moiety, selected from the library of the invention and (ii) a reporter moiety; and (b) directly or indirectly assessing the target bound probe.

Bifunctional molecular probes (comprising (i) and (ii) as described above) for use in the assay form a further aspect of the invention.

In this assay method, assessment of the binding of the bifunctional compound to any of the targets to which it is specific, that is present in the sample, may be direct or indirect. Direct and indirect assessment are well known in the field of diagnostic assays. Such procedures may involve separation of the bound (or unbound) bifunctional compound either of which may serve as the analyte. Assessment of the target molecule:bifunctional compound conjugate may be qualitative or, more preferably, quantitative and will involve direct or indirect assessment of the reporter moiety.

The assay may be directed to the assessment of a second target with the first target, in which the reporter moiety on a probe for the second target is recognized by the bifunctional compound. Thus a bifunctional compound may be directed to a probe, preferably molecular, which recognizes a further target, in which case the probe is allowed to bind to the further target under suitable binding conditions prior to the addition of the bifunctional compound as mentioned above.

To provide the probe, the specific target-binding peptide/protein:DNA conjugates may incorporate or be conjugated to a reporter moiety such that the presence within a test sample of the target of interest may be determined and/or quantified.

The peptide or protein target-binding moiety in the bifunctional compound binds to the target by virtue of a target-binding region which constitutes some or all of the amino acid residues of the expressed peptide or protein. Generally, this will correspond to at least a portion of the display moiety as previously defined.

The reporter moiety may be any moiety capable of direct or indirect detection, e.g. by virtue of its enzymatic properties, radiation emission, scattering or absorption properties, of its magnetic properties, or of its ability to cooperate with or bind to a complimentary agent to produce a detectable effect e.g. interact with an enzyme to produce a signal, gas evolution, light emission, colour change, turbidity, precipitation, etc. The reporter moiety may alternatively be any part of the peptide/protein:DNA conjugate which is recognizable and may bind a further molecule which may directly or indirectly produce a signal. Thus, for example, an antibody directed to a particular region of the genetic material or peptide/protein may be employed. The above-mentioned moieties are well known within the field of diagnostic assays.

The reporter moiety in the bifunctional compounds of the invention may be incorporated in or conjugated to the peptide/protein or DNA moiety. Thus by way of example radio-labelled amino acids or nucleotides may be used for the construction of the peptide/protein or encoding DNA, the radionuclides built into the peptide/protein or nucleic acid structures then functioning as the reporter moieties. Such labelled constituents may be incorporated during the preparation of the parent library or during subsequent screening or amplification steps where these are performed.

Alternatively a reporter molecule may be conjugated to the peptide/protein or DNA which directly or indirectly allows detection or measurement of the presence of the target to which the peptide or protein is capable of binding. Such reporter molecules include for example radiolabels, chemical labels, for example chromophores or fluorophores (e.g. dyes such as fluorescein and rhodamine), or reagents of high electron density such as ferritin, haemocyanin or colloidal gold.

Alternatively, the reporter molecule may be an enzyme, for example peroxidase or alkaline phosphatase, wherein the presence of the enzyme is visualized by its interaction with a suitable entity, for example a substrate. The enzymatic activity may be provided by the expressed protein or peptide, including the peptide or protein target-binding entity, if the target to which it binds is for example a receptor to the enzyme or a substrate therefor. Coupling of enzymes to peptides or proteins may be achieved using conventional techniques, e.g. using an activated enzyme such as activated alkaline phosphatase (Boehringer Mannheim Biochemicals).

The reporter moiety may also form part of a signalling pair wherein the other member of the pair is found on, or in close proximity to, the target to which the peptide or protein binds, for example, a fluorescent compound and a quench fluorescent substrate. As mentioned previously, the peptide/protein or DNA may also be detected by association with, or binding of, a further molecule which recognizes its identity, for example an antibody directed to part of the sequence which may form the target-binding region of the peptide/protein or a region of the peptide or protein not involved in target binding which optionally may be added for the purposes of recognition, or in the case of DNA directed against specific nucleic acid motifs. Thus the specific target-binding region may fall within a larger peptide or protein, wherein the portions of the peptide or protein not involved in binding the target may serve a structural or functional role for the expressed peptide or protein, e.g. as a scaffold sequence or may function as a reporter moiety, or as a linking group linking the specific target-binding region to a reporter moiety or to a further component of the probe, e.g. a carrier or a macromolecule.

The bifunctional compounds useful in accordance with the invention can be produced by conjugating a reporter molecule to the resulting appropriate peptide or protein, either directly or via a linker moiety. Generally this will be by reaction with an optionally activated carboxyl or amine functionality on the peptide or protein. Such conjugation reactions are well within the ability of a chemist of ordinary skill.

Alternatively, the reporter molecule may be introduced by utilizing an appropriately labelled amino acid in the construction of the peptide or protein.

The bifunctional probe compounds may be used to recognize specific targets of interest in various systems known in the art, including diagnostic assays as mentioned previously.

Figure 2:
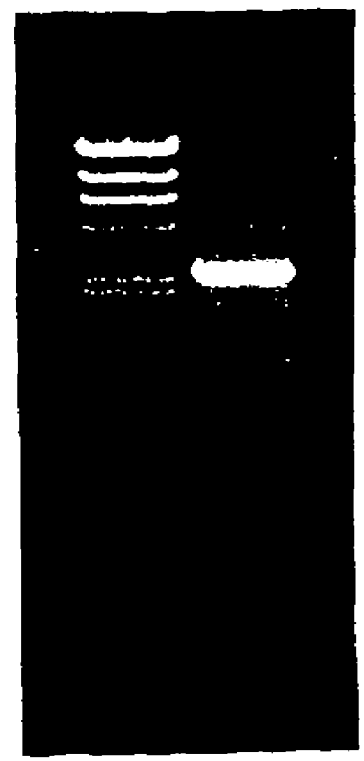

The following Examples are given by way of illustration only, with reference to the drawings in which FIG. 1 shows the construction of the pEN21 and pEN24 constructs, and FIG. 2 shows the production of DNA molecules containing a randomized region of 30 base pairs generated by PCR in which lane 1 is a marker ($\lambda$, HindIII) and lane 2 is the PCR product.

EXAMPLE 1

General Methodology for Generating an In Vitro Peptide Library and Panning for a Target Materials:
A. Plasmid or PCR fragment containing T7 promoter, ribosome binding site, the P2 A gene and T7 terminator. Such plasmids have been described by Liu & Haggård-Ljungquist (1994, supra) or may be obtained from Biotechnology Centre of Oslo, University of Oslo (BiO).
B. One primer (library primer) that contains the following sequences complementary to plasmid/fragment:
   T7 promoter,
   ribosome binding site
   30 random nucleotides (XXT/G) after the first ATG start codon, alternatively, one cysteine codon after the first start codon and after the random sequence (for constrained peptide libraries).
   approximately 20 nucleotides downstream from the first start codon complementary to the coding sequence for the P2 A gene.
Primers may be custom synthesized or obtained from BiO.
C. One PCR primer T7 promoter region (BiO).
D. One PCR primer in the T7 terminator region (counter clockwise) (BiO).
E. Target bound to solid support. Conveniently this may be performed using a biotinylated target and binding this to streptavidin or avidin on a solid support. Alternatively, avidin itself may be the "target" if avidin-binding peptides are sought. Streptavidin bound to microtiter wells or streptavidin bound to magnetic particles or Avidin-Resin may be bought from Dynal (Norway) or Promega (USA), respectively.
F. T7 S30 extract for in vitro coupled transcription/translation of linear templates may be obtained from Promega (USA).

* The rest of the material needed is standard for anyone working with molecular biology techniques.

Methods:

1. Starting with a plasmid or PCR fragment as mentioned in A, linear PCR is performed by adding the library primer mentioned in B. The exact set-up for this reaction is dependent on the primer and the same considerations that apply to PCR or cycle sequencing also apply here. This will generate a library of up to $10^{12}$ to $10^{13}$ molecules, dependent on the effectiveness of the PCR. To avoid primer competition in the next step, the remaining library primers should preferably be removed at this point by the use of a Centricon-100 column (Amicon).

2. To amplify this material, 5-7 cycles of PCR with primers C and D are performed. This is performed using the library primer extended DNA aliquoted into five portions.

3. One portion of the material from the library generated (ex. one fifth) is added to a S30 extract for linear fragments containing T7 RNA Polymerase (F) as described in the Promega manual. The reaction is incubated for 30-60 min. at 37° C. and then stopped by placing the tube(s) on ice.

4. The target is attached directly to a solid support by the biotin-streptavidin system. Avidin coupled to Resin matrix or streptavidin magnetic beads may be obtained commercially from Promega and Dynal, respectively.

5. The S30 extract is diluted 1:10 in the desired binding buffer (Sambrook et. al. (1989), Molecular Cloning: A laboratory manual, 2nd Ed., Cold Spring Harbor Laboratory Press, Cold Spring Harbor, N.Y.), and the peptide library in the S30 extract is allowed to interact with the target for 1-3 hours (or overnight). Non-binders are removed by washing 5× with 1×PBS+0.5% Tween-20 (Sigma) for 5 minutes. The bound peptide-protein A-DNA complex is eluted from the target with the desired eluant, for example biotin if the target is avidin and an avidin-binding peptide is sought. Elution with boiling $dH_2O$ may also be performed to release the complex from the target and simultaneously release the genetic material from the non-genetic material.

6. The eluted DNA is concentrated before going into the next round of PCR. This is performed most conveniently by using a Centricon-100 column and following the manufacturer's recommendations. The final volume of the eluted DNA is 50 µl. Alternatively the complex may be purified before PCR without separation of genetic and non-genetic material.

7. A new PCR reaction is set up using primers C and D with 30-40 cycles.

8. The whole procedure from step 3 to 7 is performed again, four to five times.

9. After the final cycle of elution and PCR the fragments need to be cloned in order to isolate and study individual fragments to determine their sequences. This is performed by digesting the final PCR fragment with Xba I and BamH I and ligating this to vector pET-3a (Novagene) (A) digested with the same enzymes.

10. The ligated vector is then transformed into *E. coli*. Since there are many copies of the same sequence, the efficiency of transformation is not critical.

11. Individual clones are picked and the plasmid DNA isolated by standard protocols. A final round of S30 extract and selection (steps 3 to 7) is performed to prevent binders that only act co-operatively (together with other binders).

12. The final PCR product is sequenced over the variable region, and a consensus sequence is obtained. In order to obtain a good consensus sequence, up to 50 clones should be sequenced.

13. The deduced peptide sequence is synthesised and tested separately for its binding properties.

EXAMPLE 2

A library population is obtained using a randomized base primer for amplification of the A gene. The display module which corresponds to about 3000 base pairs is shown schematically as follows for the linearized plasmid pEE709 (A gene inserted into pET8c=pET3d at the NcoI site after fill in).

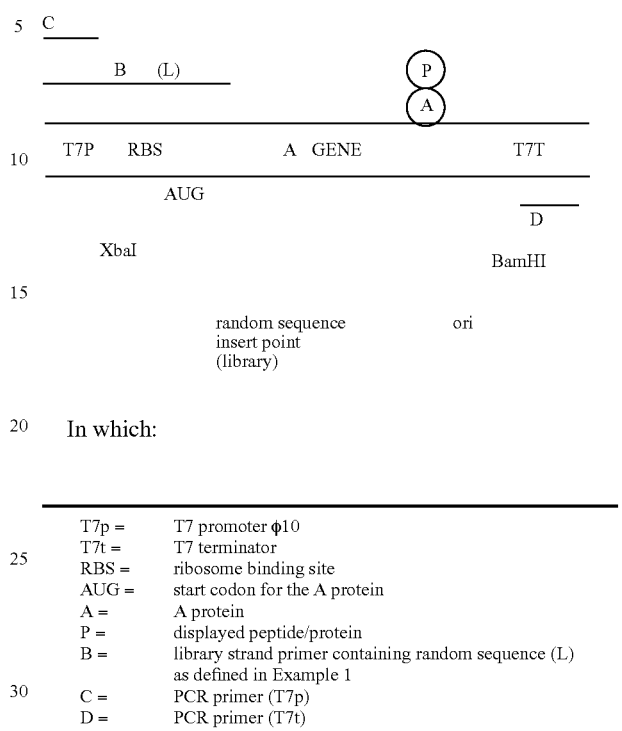

In which:

| | |
|---|---|
| T7p = | T7 promoter φ10 |
| T7t = | T7 terminator |
| RBS = | ribosome binding site |
| AUG = | start codon for the A protein |
| A = | A protein |
| P = | displayed peptide/protein |
| B = | library strand primer containing random sequence (L) as defined in Example 1 |
| C = | PCR primer (T7p) |
| D = | PCR primer (T7t) |

In the above diagram the A gene insert starts with GCC (the second codon) and ends with GCA (bases 3427-29). (See DNA sequence of Liu et al., 1993, supra).

The primers used in the Example are as follows:

B: GAAATTAATACGACTCACTATAGG-GAGACCACAACGGTTTCCCTCTAGAAA TAATTTTGTTTAACTTTAAGAAGGAGATATACCATG-[XXT/G]$_{10}$-GCCGTTAAA GCCTCCGGG [135 nucleotides]

C: GAAATTAATACGACTCACTATAGGG

D: CAAAAAACCCCTCAAGACCCG

1. Generation of a Peptide Library

A DNA fragment population with a set of randomized bases is obtained as follows:

Linear amplification (or primer extension) is performed on the linearized (HindIII) plasmid pEE709 by the library primer B. The reaction mixture of 100 µl contains: 0.3 g plasmid DNA (about $6\times10^{10}$ molecules or 0.1 µmol), 5 µg library primer DNA (about $7\times10^{13}$ molecules or 125 pmol) and the rest of the ingredients as described for the PCR reaction below. The mixture is subjected to 5 cycles of PCR as described below. The library primer is preferably removed using a Centricon-100. The library primer extended DNA (library) is diluted and subdivided into five 100 µl (final volume) aliquots and subjected to a limited PCR (5 cycles) using primers C and D. Each reaction mixture contains: 0.6 µg library primer extended DNA, 125 pmol of the respective primers C and D, 0.2 mM of each dNTP, 50 mM KCl, 4 mM $MgCl_2$, 10 mM Tris-HCl (pH 9.0 at 25° C.), 0.1% Triton X-100 and 2.5 U Taq DNA polymerase (Promega) in a final volume of 100 µl. The mixture is subjected to 35 cycles of 1 minute at 94° C., 2 minutes at 42° C. and 3 minutes at 72° C.

in a thermocycler (Perkin Elmer model PCR1000). The PCR product is purified by removal of the primers (Centricon-100), phenol treatment and ethanol precipitation. At this point the library should comprise $10^{12}$ to $10^{13}$ DNA molecules.

An alternative library approach would simply be to run PCR cycles on the vector fragment DNA using the library primers B and D to drive the PCR.

2. In Vitro Translation and Screening for an Avidin Binding Peptide

A. A combination of Promega's T7 S30 and S30 linear template extract is used for coupled transcription/translation of linear DNA templates. Transcription of the A gene is driven by the T7 RNA polymerase from the T7 promoter ø10. One of the five DNA library sets which is phenol treated and precipitated by ethanol is resuspended in 9 µl distilled water. To this volume are added the ingredients (5 µl of aminoacid mix, 20 µl of S30 pre-mix, 1 µl of T7 S30 and 15 µl of S30 for linear templates) of the S30 protocol (Promega) to make a final volume of 50 µl. The coupled transcription/translation process is allowed to proceed for 60 minutes (or as long as required) at 37° C.

B. The reaction mixture (50 µl) is added to 50 µl SoftLink Avidin Resin (Promega) and allowed to mix for 2 hours at room temperature for the panning of peptides binding to Avidin. The Resin is pelleted by centrifugation (10000 rev/min for 5 minutes) and washed (five times with PBS, 20 mM $Na_2HPO_4$, 100 mM NaCl pH 7.5). Potential avidin binders are eluted with 5 mM biotin or simply by subjecting the entire avidin-Resin complex to PCR with primers C and D as described in 1A. The PCR product is separated from the avidin-Resin by centrifugation, phenol treated and precipitated by ethanol before being subjected to a new coupled transcription/translation and panning cycle. Cycles of peptide display and panning can be repeated until the anticipated peptide enrichment has been achieved. Polyclonal antibodies specific for the A protein can be used to monitor the presence and increase of the protein A carrier during the panning. After the fourth round of panning the final PCR product is cut with restriction enzymes XbaI and BamHI and inserted into pET-3a (cut with the same enzymes) by ligation. After transformations, individual colonies are isolated and plasmids extracted for sequence determination of the insert in order to obtain the amino acid sequence of the peptide.

EXAMPLE 3

A peptide library is prepared and screened as described in Example 2, but prior to translation (step 2), the DNA molecules are purified and then circularized with T4 DNA ligase (New England Biolabs), according to the manufacturer's instructions in accordance with standard protocols (see Sambrook, 1989, supra).

In this case, hybridization conditions need not be maintained during screening and thus may be performed in for example, 1% Triton X-100, 0.5 M KOAc or 1% Triton X-100, 350 mM NaCl, 5% glycerol which are conditions suitable for screening for SRP receptor heterodimerization, or in 1% Triton X-100, 2M urea, 100 mM NaCl, 50 mM Tris HCl pH 7.5 or 1% Triton X-100, 0.1% SDS, 100 mM NaCl, 50 mM Tris HCl pH 7.5, which conditions are suitable for screening antibody:antigen interactions.

EXAMPLE 4

Demonstration of the in vitro cis-action of the P2 DNA replication initiation protein A.

Experiment 1

An equal amount of DNA of two plasmids carrying the P2 A gene (pEE709; carries also an amp resistance gene, Liu and Haggard-Ljungquist, 1994, supra) and the P2 A gene fused to a stretch of six histidines at the very N-terminal end of A (pEE711; carries also an amp resistance gene, Liu and Haggard-Ljungquist, 1994, supra) were subjected to a coupled transcription/translation reaction in a S30-T7 extract (Promega, USA). The presence of the histidine stretch transforms the A protein into a Ni binding protein. Hence the His::A expressing plasmid pEE711 should selectively bind to a Ni-containing solid support if the A protein is cis-acting in the S30-T7 extract. In both plasmid constructs transcription of the A gene is under control of phage T7 Ø10 promoter. After translation the extent of binding to a Ni-column was determined.

Materials and Methods

One ug of DNA of the pEE709 and the pEE711 plasmids respectively was added to the coupled transcription/translation extract kit (20 ul S30 premix, 5 ul aminoacid mix and 15 ul *E. Coli* T7 S30 extract system for circular DNA, Promega, USA). The transcription/translation was allowed to proceed for 60 minutes at 37° C. The extract mixture was diluted 12-fold in washing buffer (Qiagen; Buffer 11-50 mM Na-phosphate pH 8.0, 300 mM NaCl, 20 mM imidazole, 1 mM PMSF) and subjected to Ni selection by addition to a Ni-NTA spin column (Qiagen, Germany) equilibrated with Buffer 1 (50 mM Na-phosphate pH 8.0, 300 mM NaCl, 20 mM imidazole) under non-denaturing conditions. Washing was done three times with 600 ul Buffer 11 and elution was performed twice by 250 ul Buffer 111 (50 mM Na-phosphate pH 8.0, 300 mM Nacl, 250 mM imidazole) as recommended by the manufacturer (see protocol for Ni-NTA Spin kit, Qiagen, Germany, spring 1994). A standard table top centrifuge was used to spin the Ni-columns for 2 minutes at 2000 rpm during washing and elution. High efficiency competent cells JM109 (Promega, USA) were transformed with a portion of the eluant and scored for ampicillin resistant colonies. Plasmids of individual colonies were isolated and type characterized by agarose gel electrophoresis.

To determine the distribution (ratio) of the plasmid types in the eluant, the presence of plasmids was measured by transformation of strain JM 109 (Promega) for amp-resistance. Colonies were picked and analysed for their plasmid type (differentiated by size) after plasmid extraction followed by agarose gel electrophoresis. The ratio of pEE711 (His::A) to pEE709 (A) in the absence of Ni-column selection was also determined.

Results:

The results which were obtained are shown in the Table below:

| Ratio of His:A/A plasmids in the absence of Ni selection | Ratio of His:A/A plasmids after Ni selection (average of 4 experiments) | Enrichment of the His:A plasmid relative to the A plasmid after Ni selection |
|---|---|---|
| 0.7 | 9.3 | 13.3 |

Experiment 2

In the second experiment two new plasmid constructs pEN21 (an A gene construct with an amp resistance gene, see FIG. 1) and pEN24 (a His::A gene construct with a tag of six histidine residues and a kanamycin resistance gene, see FIG. 1) were subjected to the same type of experiment as in experiment 1 above, with the modifications indicated in the materials and methods section below. By employing this differential antibiotic resistance it is possible to score for the individual plasmid types directly as bacterial colonies.

Materials and Methods pEN21 and 24 are derivatives of pET21a and pET24a (Novagen Inc. USA). The pET21a and pET24a vectors differ only by their selectable marker (ampicillin and kanamycin resistance respectively). The pEN21 and pEN24 were constructed by restriction cutting of pEE709 and pEE711 with XbaI and BlpI which cuts out the A gene and flanking regions. pET21a and pET24a were cut with the same restriction enzymes. The A-fragments and new vector fragments were isolated from an agarose gel after electrophoresis by Spin-Bind columns (FMC). The A-fragment from pEE709 was cloned into the pET21a vector and the His-A-fragment was cloned into pET24a vector. The plasmids were incubated for 30 minutes in the S30 extracts and the plasmid types were scored by differential antibiotic resistance using ampicillin (pEN21) and kanamycin (pEN24) plates after transformation of E. coli strain BK 2118 by electroporation. Buffer 11 was here modified to contain 1 mM imidazole rather than 20 mM imidazole and the protease inhibitor PMSF omitted, called Buffer 11*). The Ni-NTA spin column was equilibrated by washing buffer (Buffer 11* non-denaturing conditions). Washing was done three times with 600 ul Buffer 11* and elution was performed twice by 250 ul Buffer 111 as recommended by the manufacturer (see protocol for Ni-NTA Spin kit, Qiagen, Germany, spring 1994). A plasmid mixture of equal amounts of pEN21 and pEN24 DNA, which had not been exposed to the S30 extract, was subjected to Ni-selection as a control.

Results:

The results are shown in the Table below.

| Ratio of His:A/A plasmids in the extract prior to Ni selection (average of 10 experiments) | Ratio of His:A/A plasmids after Ni selection (average of 10 experiments) | Enrichment of the His:A plasmid relative to the A plasmid after Ni selection |
|---|---|---|
| 0.5 | 3.4 | 6.8 |

In the case when the S30 extract was omitted and the pure plasmid mixture was subjected to the Ni-column no enrichment was observed.

Conclusions:

As expected in all experiments the ratio of His:A/A plasmids in the absence of Ni selection was approximately 1. In contrast, the ratio of His::A/A plasmids after Ni selection (approximately 9.3 and 3.4) lead to enrichment of the His::A plasmids of approximately 13 and 7 respectively. To determine if these numbers demonstrate efficient cis action of the His tagged P2 A in vitro it is necessary to compare these values for enrichment to the enrichment which could theoretically be obtained using the experimental conditions employed above. To permit comparison of the experimental data with the theoretical values we measured non-specific background in the eluant fractions and estimated the amount of His::A synthesized in the transcription/translation reaction.

The non-specific background remaining in the samples was measured by performing a nickel column selection on plasmids without translation in E. coli lysate. One third of the eluant was transformed into E. coli and the resulting colonies were counted. Using the measured transformation efficiency for the E. coli cells used we then calculated that the eluant contains 0.3 fmol of each plasmid in the absence of His tagged P2 A protein.

It is estimated that approximately 5 fmol ($3 \times 10^9$ molecules) of protein A was synthesized in our standard reaction. Thus assuming that every His::A molecule synthesized bound to an encoding DNA molecule the enrichment obtained would be $(5+0.3)/0.3=18$. The average enrichment obtained in the two experiments was $(13+7)/2=10$. Thus we interpret these results to mean that the P2 A protein is able to efficiently function in cis in vitro as well as to display a stretch of six histidines fused to its very N terminal. Despite poor translation efficiency in the present experiments it is expected that a library with $10^{12}$ members may be obtained. It is furthermore anticipated that additional or more vigorous washing will improve enrichment thereby aiding the production of libraries of the invention.

Experiment 5

DNA molecules to be used for the expression of a peptide library of the invention were prepared.

Materials and Methods

DNA molecules to be used for expressing the in vitro peptide display library were prepared by amplification of the A gene from the linearized plasmid pEN21 (see FIG. 1 and Example 4) using the following primers:

B: 5'CGA TCC CGC GAA ATT AAT ACG ACT CAC TAT AGG GAG ACC ACA ACG GTT TCC Ctc tag aAA TAA TTT TGT TTA ACT TTA AGA AGG AGA TAT ACC ATG (NNT/G)$_{10}$ GCC GTT AAA GCC TCC GGG 3' [144 nucleotides, with a region of 30 randomized bases and a unique XbaI site (small letters) which corresponds to primer B in Example 2 with the addition of 9 5' nucleotides]

C: 5' AGA TCT CGA TCC CGC GAA ATT AAT ACG ACT CAC TAT AGG G 3' [40 base primer complementary to the upstream area of plasmid pEN21, covering the T7 promoter as well as bases upstream of the T7 promoter which corresponds to primer C in Example 2 with the addition of 15 5' nucleotides]

D: 5'CAA AAA ACC CCT CAA GAC CCG 3' [21 base primer complementary to a sequence downstream of the T7 terminator and corresponding to primer D in Example 2]

The primers were synthesized in an Applied Biosystems 394 DNA/RNA synthesizer and checked by polyacrylamide gel electrophoresis. The library primer displayed heterogeneity on the gel due to its randomized nature.

Primers B and D were used to prepare the DNA molecules of the library in a PCR reaction (performed similar to the PCR reaction described in Example 2) using 5 µl polymerase buffer (10× Vent pol. Buffer, New England Biolabs), 50 µmol primer B, 20 µmol primer D, long DNA template (pEN21), 1 µl dNTP-mix (10 mM, New England Biolabs), 1 µl Deep Vent polymerase (New England Biolabs), all in a total volume of 50A1, with a hotstart of 94° C. for 5 minutes, an annealing temperature of 55° C. for 30 seconds (post-annealing at 58° C. for 2 minutes), a polymerisation temperature of 74° C. for 2 minutes (post-polymerisation at 74° C. for 7 minutes) for 25 rounds.

Primer C is used to further amplify the library (and remove heteroduplex molecules) in the absence of the library primer B. It is advisable to remove primer B by purification prior to this amplification step.

Results:

A DNA display module of approximately 3000 base pairs was produced with a randomized sequence of 30 bases at the 5' end of the A gene (following the start codon ATG). The PCR product which constitutes the library is shown in FIG. 2.

The invention claimed is:

1. A method of producing a peptide or protein expression library in vitro which displays a population of peptides or proteins, wherein the peptides or proteins are specifically associated with the DNA encoding them through covalent binding of the peptides or proteins to the encoding DNA, said method comprising at least the following steps:
   1) preparing a genetic library of a population of DNA molecules, each DNA molecule comprising:
      (a) a nucleotide sequence encoding a binding moiety comprising an amino acid sequence which is a cis-acting DNA binding protein which binds specifically to the DNA encoding sequence through covalent binding of the amino acid sequence to DNA, and
      (b) a nucleotide sequence encoding a display moiety comprising an amino acid sequence for display, and wherein the display moiety comprises at least one site of attachment for the binding moiety, and
   2) expressing the genetic library thus formed whereby the population of peptides or proteins is produced each specifically associated with the DNA encoding sequence through covalent binding.

2. The method as claimed in claim 1 wherein expression of the genetic library is performed in vitro in a cellular system with at least one copy of a single library member expressed per host cell or organism.

3. The method as claimed in claim 1 wherein expression of the genetic library is performed in vitro, and is cell-free expression.

4. The method as claimed in claim 1 wherein said cis-acting protein is the P2 A protein.

5. The method as claimed in claim 3 wherein said expression is performed in the presence of a mis-match oligonucleotide which hybridizes to the DNA adjacent to the attachment site on both sides but that does not hybridize to the attachment site.

6. The method as claimed in claim 1 wherein said amino acid sequence for display is up to 40 amino acid residues.

7. The method as claimed in claim 1 wherein said amino acid sequence for display is generated by, or comprises DNA fragments from, cloning.

8. A method as claimed in claim 1 wherein said binding moiety is P2A modified by replacement of tyrosine at amino acid position 450 with phenylalanine.

9. A method of identifying a specific target-binding peptide or protein, said method comprising:
   a) contacting a peptide expression library produced according to the method of claim 1 with a target molecule,
   b) selecting and isolating a library member that binds to said target molecule, and
   c) isolating from said library member the peptide or protein that is bound to said target molecule.

10. The method as claimed in claim 9 further comprising isolating from said library member the DNA sequence encoding the peptide or protein that binds specifically to said target molecule.

11. A method of assaying for the presence of a target molecule in a sample, said method comprising
   (a) contacting said sample with a molecular probe comprising
      (i) a peptide or protein target-binding moiety that selectively binds to said target molecule, wherein said target-binding moiety is covalently bound to DNA encoding said target-binding moiety and
      (ii) a reporter moiety
   wherein said contacting is effected under conditions such that said target-binding moiety can bind target molecule present in said sample selectively; and
   (b) detecting the presence of reporter moiety bound to said target-bound molecular probe.

12. The method according to claim 1, wherein said nucleic acid encoding said amino acid sequence for display is generated by amplification by PCR.

13. The method according to claim 1 wherein the cis-acting protein is φX174.

* * * * *